United States Patent [19]

Scanlan et al.

[11] Patent Number: 6,043,084
[45] Date of Patent: Mar. 28, 2000

[54] ISOLATED NUCLEIC ACID MOLECULES ASSOCIATED WITH COLON CANCER AND METHODS FOR DIAGNOSING AND TREATING COLON CANCER

[75] Inventors: Matthew J. Scanlan; Yao-Tseng Chen; Elisabeth Stockert; Lloyd J. Old, all of New York, N.Y.

[73] Assignee: Ludwig Institute for Cancer Research, New York, N.Y.

[21] Appl. No.: 08/948,705

[22] Filed: Oct. 10, 1997

[51] Int. Cl.[7] .............................. C12N 5/10; C12N 15/12; C12N 15/63
[52] U.S. Cl. ................. 435/325; 435/252.3; 435/254.11; 435/320.1; 435/419; 536/23.5
[58] Field of Search ........................... 435/252.3, 254.11, 435/325, 320.1, 419; 536/23.5

[56] References Cited

U.S. PATENT DOCUMENTS 5,698,396  12/1997  Pfeundschuh ................................ 435/6

FOREIGN PATENT DOCUMENTS

WO9640209  12/1996  WIPO .

OTHER PUBLICATIONS

Genbank Accession No. N51485. yz04e06.s1 *Homo sapiens* cDNA clone 282082 3', Feb. 14, 1996.
de Plaen et al., *Proc. Natl. Sci. USA* 85:2275, 1988.
Mandelboim, et al., *Nature* 369:69 1994.
van der Bruggen et al., *Science* 254:1643–1647, 1991.
Brichard et al., *J. Exp. Med.* 178:489–495, 1993.
Coulie et al., *J. Exp. Med.* 180:35–42, 1994.
Kawakami et al., *Proc. Natl. Acad. Sci. USA* 91:3515–3519, 1994.
Oettgen et al., *Immunol. Allerg. Clin. North. Am.* 10:607–637, 1990.
Sahin et al., *Proc. Natl. Acad. Sci. USA* 92:11810–11913, 1995.
Crew et al., *EMBO J* 144:2333–2340, 1995.

*Primary Examiner*—John S. Brusca
*Attorney, Agent, or Firm*—Wolf, Greenfield & Sacks, P.C.

[57] ABSTRACT

Various molecules associated with disorders such as colon cancer are disclosed. The invention also discloses diagnostic and therapeutic methods based upon these molecules.

16 Claims, No Drawings

SEQUENCE LISTING

```
<160> NUMBER OF SEQ ID NOS: 8

<210> SEQ ID NO 1
<211> LENGTH: 1552
<212> TYPE: DNA
<213> ORGANISM: Homo Sapiens

<400> SEQUENCE: 1
cttctggatg catccgagaa gctaaaactt acttatgagg aaaagtgtga aattgaggaa      60
tcccaattga agtttttgag gaacgactta gctgaatatc agagaacttg tgaagatctt     120
aaagagcaac taaagcataa agaatttctt ctggctgcta atacttgtaa ccgtgttggt     180
ggtctttgtt tgaaatgtgc tcagcatgaa gctgttcttt cccaaaccca tactaatgtt     240
catatgcaga ccatcgaaag actggttaaa gaaagagatg acttgatgtc tgcactagtt     300
tccgtaagga gcagcttggc agatacgcag caaagagaag caagtgctta tgaacaggtg     360
aaacaagttt tgcaaatatc tgaggaagcc aattttgaaa aaaccaaggc tttaatccag     420
tgtgaccagt tgaggaagga gctggagagg caggcggagc gacttgaaaa agaacttgca     480
tctcagcaag agaaaagggc cattgagaaa gacatgatga aaaaggaaat aacgaaagaa     540
agggagtaca tgggatcaaa gatgttgatc ttgtctcaga atattgccca actggaggcc     600
caggtggaaa aggttacaaa ggaaaagatt tcagctatta atcaactgga ggaaattcaa     660
agccagctgg cttctcggga aatggatgtc acaaaggtgt gtggagaaat gcgctatcag     720
ctgaataaaa ccaacatgga gaaggatgag gcagaaaagg agcacagaga gttcagagca     780
aaaactaaca gggatcttga aattaaagat caggaaatag agaaattgag aatagaactg     840
gatgaaagca acaacactt ggaacaggag cagcagaagg cagccctggc cagagaggag     900
```

-continued

| | |
|---|---|
| tgcctgagac taacagaact gctgggcgaa tctgagcacc aactgcacct caccagatct | 960 |
| gaaatagctc aactcagtca agaaaaaagg tatacatatg ataaattggg aaagttacag | 1020 |
| agaagaaatg aagaattgga ggaacagtgt gtccagcatg ggagagtaca tgagacgatg | 1080 |
| aagcaaaggc taaggcagct ggataagcac agccaggcca cagcccagca gctggtgcag | 1140 |
| ctcctcagca agcagaacca gcttctcctg gagaggcaga gcctgtcgga agaggtggac | 1200 |
| cggctgcgga cccagttacc cagcatgcca caatctgatt gctgacctgg atggaacaga | 1260 |
| gtgaaataaa tgaattacaa agagatattt acattcatct ggtttagact taatatgcca | 1320 |
| caacgcacca cgaccttccc agggtgacac cgcctcagcc tgcagtgggg ctggtcctca | 1380 |
| tcaacgcggg cgctgtcccc gcacgcagtc gggctggagc tggagtctga ctctagctga | 1440 |
| gcagactcct ggtgtatgtt ttcagaaatg gcttgaagtt atgtgtttaa atctgctcat | 1500 |
| tcgtatgcta ggttatacat atgattttca ataaatgaac tttttaaaga aa | 1552 |

<210> SEQ ID NO 2
<211> LENGTH: 2885
<212> TYPE: DNA
<213> ORGANISM: Homo Sapiens

<400> SEQUENCE: 2

| | |
|---|---|
| ggaattcctc ttgtcgaagt caaggagcc cacaccaggc ggcctcaacc attccctccc | 60 |
| acagcacccc aaatgctggg gagcccacca tgcttctttg gaccagagtt cccctccccca | 120 |
| gagcggcccc cctgggacgc ctccctccta caaactgcct ttgcctgggc cctacgacag | 180 |
| tcgagacgac ttccccctcc gcaaaacagc ctctgaaccc aacttgaaag tgcgttcaag | 240 |
| gctaaaacag aaggtggctg agcggagaag cagtcccctc ctgcgtcgca aggatgggac | 300 |
| tgttattagc acctttaaga agagagctgt tgagatcaca ggtgccgggc ctggggcgtc | 360 |
| gtccgtgtgt aacagcgcac ccggctccgg ccccagctct cccaacagct cccacagcac | 420 |
| catcgctgag aatggctttta ctggctcagt ccccaacatc cccactgaga tgctccctca | 480 |
| gcaccgagcc ctccctctgg acagctcccc caaccagttc agcctctaca cgtctccttc | 540 |
| tctgcccaac atctccctag ggctgcaggc cacggtcact gtcaccaact cacacctcac | 600 |
| tgcctcccccg aagctgtcga cacagcagga ggccgagagg caggccctcc agtccctgcg | 660 |
| gcagggtggc acgctgaccg gcaagttcat gagcacatcc tctattcctg gctgcctgct | 720 |
| gggcgtggca ctggagggcg acgggagccc ccacgggcat gcctccctgc tgcagcatgt | 780 |
| gctgttgctg gagcaggccc ggcagcagag caccctcatt gctgtgccac tccacgggca | 840 |
| gtccccacta gtgacgggtg aacgtgtggc caccagcatg cggacggtag gcaagctccc | 900 |
| gcggcatcgg ccctgagcc gcactcagtc ctcaccgctg ccgcagagtc cccaggccct | 960 |
| gcagcagctg gtcatgcaac aacagcacca gcagttcctg gagaagcaga gcagcagca | 1020 |
| gctacagctg ggcaagatcc tcaccaagac aggggagctg cccaggcagc ccaccaccca | 1080 |
| ccctgaggag acagaggagg agctgacgga gcagcaggag gtcttgctgg gggagggagc | 1140 |
| cctgaccatg ccccggggagg gctccacaga gagtgagagc acacaggaag acctggagga | 1200 |
| ggaggacgag gaagaggatg gggaggagga ggaggattgc atccaggtta aggacgagga | 1260 |
| gggcgagagt ggtgctgagg aggggcccga cttggaggag cctggtgctg gatacaaaaa | 1320 |
| actgttctca gatgcccaac cgctgcaacc tttgcaggtg taccaagcgc ccctcagcct | 1380 |
| ggccactgtg ccccaccaag ccctgggccg tacccaatcc tccctgctg cccctggggg | 1440 |

-continued

```
catgaagaac cccccagacc aacccgtcaa gcacctcttc accacaagtg tggtctacga    1500
cacgttcatg ctaaagcacc agtgcatgtg cgggaacaca cacgtgcacc ctgagcatgc    1560
tggccggatc cagagcatct ggtcccggct gcaggagaca ggcctgctta gcaagtgcga    1620
gcggatccga ggtcgcaaag ccacgctaga tgagatccag acagtgcact ctgaatacca    1680
caccctgctc tatgggacca gtcccctcaa ccggcagaag ctagacagca agaagttgct    1740
cggtcccatc agccagaaga tgtatgctgt gctgccttgt gggggcatcg gggtggacag    1800
tgacaccgtg tggaatgaga tgcactcctc cagtgctgtg cgcatggcag tgggctgcct    1860
gctggagctg gccttcaagg tggctgcagg agagctcaag aatggatttg ccatcatccg    1920 gccccccagga caccacgccg aggaatccac agccatggga ttctgcttct tcaactctgt    1980
agccatcacc gcaaaactcc tacagcagaa gttgaacgtg ggcaaggtcc tcatcgtgga    2040
ctgggacatt caccatggca atggcaccca gcaggcgttc tacaatgacc cctctgtgct    2100
ctacatctct ctgcatcgct atgacaacgg gaacttcttt ccaggctctg gggctcctga    2160
agaggttggt ggaggaccag gcgtgggggta caatgtgaac gtggcatgga caggaggtgt    2220 ggacccccc attggagacg tggagtacct tacagccttc aggacagtgg tgatgccat     2280 tgcccacgag ttctcacctg atgtggtcct agtctccgcc gggtttgatg ctgttgaagg    2340
acatctgtct cctctgggtg gctactctgt caccgccaga tgttttggcc acttgaccag    2400
gcagctgatg accctggcag ggggccgggt ggtgctggcc ctggagggag gccatgactt    2460
gaccgccatc tgtgatgcct ctgaagcttg tgtctcggct ctgctcagtg taaagctgca    2520
gcccttggat gaggcagtct tgcagcaaaa gcccaacatc aacgcagtgg ccacgctaga    2580
gaaagtcatc gagatccaga gcaaacactg gagctgtgtg cagaagttcg ccgctggtct    2640
gggccggtcc ctgcgagggg cccaagcagg tgagaccgaa gaagccgaaa tgtgaacgcc    2700
atggccttgc tgttggtggg ggccgaacag gcccaagctg cggcagcccg ggaacacagc    2760
cccaggccgg cagaggagcc catggagcag gagcctgccc tgtgacgccc cggcccccat    2820 cccttgggc ttcaccattg tgattttgtt tatttttct attaaaaaca aaagttaaa      2880 aattt                                                                2885
```

```
<210> SEQ ID NO 3
<211> LENGTH: 1298
<212> TYPE: DNA
<213> ORGANISM: Homo Sapiens
<220> FEATURE:
<221> NAME/KEY: unsure
<222> LOCATION: 55..55
<223> OTHER INFORMATION:
<220> FEATURE:
<221> NAME/KEY: unsure
<222> LOCATION: 141..141
<223> OTHER INFORMATION:
<220> FEATURE:
<221> NAME/KEY: unsure
<222> LOCATION: 199..99
<223> OTHER INFORMATION:
<220> FEATURE:
<221> NAME/KEY: unsure
<222> LOCATION: 342..342
<223> OTHER INFORMATION:
<220> FEATURE:
<221> NAME/KEY: unsure
<222> LOCATION: 352..352
<223> OTHER INFORMATION:
<220> FEATURE:
<221> NAME/KEY: unsure
<222> LOCATION: 722..722
<223> OTHER INFORMATION:
```

-continued

```
<220> FEATURE:
<221> NAME/KEY: unsure
<222> LOCATION: 750..750
<223> OTHER INFORMATION:
<220> FEATURE:
<221> NAME/KEY: unsure
<222> LOCATION: 1058..1058
<223> OTHER INFORMATION:
<220> FEATURE:
<221> NAME/KEY: unsure
<222> LOCATION: 1101..1101
<223> OTHER INFORMATION:
<220> FEATURE:
<221> NAME/KEY: unsure
<222> LOCATION: 1144..1144
<223> OTHER INFORMATION:

<400> SEQUENCE: 3
ggctgctgaa atgactgcga accggcttgc agagagcctt ctggctttga gccancagga      60
agaactagcg gatttgccaa agactacct cttgagtgag agtgaagatg aggggggacaa    120 tgatggagag agaaagcatc naaagcttct ggaagcaatc agttcccttg atggaaagaa    180
taggcggaaa ttggctgana ggtctgaggc tagtctgaag gtgtcagagt tcaatgtcag    240
ttctgaagga tcaggagaaa agctggtcct tgcagatctg cttgagcctg ttaaaacttc    300
atcttctttg gccactgtga aaaagcaact gagtagagtc anatcaaaga anacagtgga    360
gttacctctg aacaaagaag agattgaacg gatccacaga gaatagcatt caataaaacg    420
cacaagtcct ctccaaatgg gaccctgtcg tcctgaagaa ccggcaggca gagcagctgg    480
tttttcccct ggagaaagag gagccagcca ttgctcccat tgaacatgtg ctcagtggct    540
ggaaggcaag aactcccctg gagcaggaaa ttttcaacct cctccataag aacaagcagc    600
cagtgacaga ccctttactg acccctgtgg aaaaggcctc tctccgagcc atgagcctag    660
aagaggcaaa gatgcgacga gcagagcttc agagggctcg ggctctgcag tcctactatg    720
angccaaggc tcgaagagag aagaaaatcn aaagttaaaa gtatcacaaa gtcgtgaaga    780
aaggaaaggc caagaaagcc ctaaaagagt ttgagcagct gcggaaggtt aatccagctg    840
ccgcactaga agaacgaaga aaagaggaaa gaaggaggag gagaaagaag aagaacaagg    900
agaagaagaa agaagaaggg agaaggagaa gaaaagaagg agaagaggaa aaggaagaag    960
gagaaagaaa aggagaagga aaaggaaaag aaggagaaga aagaagaact aagaagaagg   1020
agaggaagaa taagaaggaa agaagaaaga aaaaagtnaa agaagaagaa agaaggaaga   1080
aggaaagaag aggaagaact nagaagaaga aagaggagga agaagaaag aagaataagg    1140 aacnagaaag aaggagaaga aagaataaga agaggaagaa gaaaaagaag aaaagaagaa   1200
ggaaagaagg agaaaaagga agaaaaaagg aagaagaaag tagaaagcgg aagaaagaaa   1260
agaaagtata agaaggaaga agaagaaaga aggaaaaa                            1298

<210> SEQ ID NO 4
<211> LENGTH: 2236
<212> TYPE: DNA
<213> ORGANISM: Homo Sapiens

<400> SEQUENCE: 4
cctggcccgg tcgcggtcgc ggctctttcc agctcctggc agccgggcac ccgaaggaac    60
gggtcgtgca acgacgcagc tggacctggc ccagccatgg accgaaaagt ggcccgagaa   120
ttccggcata aggtggattt tctgattgaa aatgatgcag agaaggacta tctctatgat   180
gtgctgcgaa tgtaccacca gaccatggac gtggccgtgc tcgtgggaga cctgaagctg   240
```

-continued

```
gtcatcaatg aacccagccg tctgcctctg tttgatgcca ttcggccgct gatcccactg      300
aagcaccagg tggaatatga tcagctgacc ccccggcgct ccaggaagct gaaggaggtg      360
cgtctggacc gtctgcaccc cgaaggcctc ggcctgagtg tgcgtggtgg cctggagttt      420
ggctgtgggc tcttcatctc ccacctcatc aaaggcggtc aggcagacag cgtcgggctc      480
caggtagggg acgagatcgt ccggatcaat ggatattcca tctcctcctg tacccatgag      540
gaggtcatca acctcattcg aaccaagaaa actgtgtcca tcaaagtgag acacatcggc      600
ctgatccccg tgaaaagctc tcctgatgag cccctcactt ggcagtatgt ggatcagttt      660
gtgtcggaat ctgggggcgt gcgaggcagc ctgggctccc ctggaaatcg ggaaaacaag      720
gagaagaagg tcttcatcag cctggtaggc tcccgaggcc ttggctgcag catttccagc      780
ggccccatcc agaagcctgg catctttatc agccatgtga acctggctc cctgtctgct       840 gaggtgggat tggagatagg ggaccagatt gtcgaagtca atggcgtcga cttctctaac      900
ctggatcaca aggaggctgt aaatgtgctg aaaaatagcc gcagcctgac catctccatt      960
gtagctgcag ctggccggga gctgttcatg acagaccggg agcggctggc agaggcgcgg     1020
cagcgtgagc tgcagcggca ggagcttctc atgcagaagc ggctggcgat ggagtccaac     1080
aagatcctcc aggagcagca ggagatggag cggcaaagga gaaagaaat tgcccagaag      1140 gcagcagagg aaaatgagag ataccggaag gagatggaac agattgtaga ggaggaagag     1200
aagtttaaga gcaatgggga agaagactgg ggctcaaagg aacagctact cttgcctaaa     1260
accatcactg ctgaggtaca cccagtaccc cttcgcaagc caaagtatga tcaggagtg      1320 gaacctgagc tcgagcccgc agatgacctg gatggaggca cggaggagca gggagagcag     1380
gatttccgga aatatgagga aggctttgac ccctactcta tgttcacccc agagcagatc     1440
atggggaagg atgtccggct cctacgcatc aagaaggagg atccttaga cctggccctg      1500 gaaggcggtg tggactcccc cattgggaag gtggtcgttt ctgctgtgta tgagcgggga     1560
gctgctgagc ggcatggtgg cattgtgaaa ggggacgaga tcatggcaat caacggcaag     1620
attgtgacag actacaccct ggctgaggct gacgctgccc tgcagaaggc ctggaatcag     1680 ggcgggggact ggatcgacct tgtggttgcc gtctgccccc caaggagta tgacgatgag     1740 ctgaccttct tgctgaagtc caaaagggga aaccaaattc acgcgttagg aaacagtgag     1800
ctccggcccc acctcgtgaa cacaaagcct cggaccagcc ttgagagagg ccacatgaca     1860
cacaccagat ggcatccttg ggacctgaat ctatcaccca ggaatctcaa actccctttg     1920
gccctgaacc agggccagat aaggaacagc tcgggccact ttttgaagg ccaatgtgga      1980 ggaaagggag cagccagccg tttgggagaa gatctcaagg atccagactc tcattccttt     2040
cctctggccc agtgaatttg gtctctccca gctttggggg actccttcct tgaaccctaa     2100
taagacccca ctggagtctc tctctctcca tccctctcct ctgccctctg ctctaattgc     2160
tgccaggatt gtcactccaa accttactct gagctcatta ataaaataaa cagatttatt     2220
ttccagctta aaaaa                                                      2236
```

<210> SEQ ID NO 5
<211> LENGTH: 2162
<212> TYPE: DNA
<213> ORGANISM: Homo Sapiens

<400> SEQUENCE: 5

```
cctggcccgg tcgcggtcgc ggctctttcc agctcctggc agccgggcac ccgaaggaac       60
gggtcgtgca acgacgcagc tggacctggc ccagccatgg accgaaaagt ggcccgagaa      120
```

```
ttccggcata aggtggattt tctgattgaa aatgatgcag agaaggacta tctctatgat    180
gtgctgcgaa tgtaccacca gaccatggac gtggccgtgc tcgtgggaga cctgaagctg    240
gtcatcaatg aacccagccg tctgcctctg tttgatgcca ttcggccgct gatcccactg    300
aagcaccagg tggaatatga tcagctgacc ccccggcgct ccaggaagct gaaggaggtg    360
cgtctggacc gtctgcaccc cgaaggcctc ggcctgagtg tgcgtggtgg cctggagttt    420
ggctgtgggc tcttcatctc ccacctcatc aaaggcggtc aggcagacag cgtcgggctc    480
caggtagggg acgagatcgt ccggatcaat ggatattcca tctcctcctg tacccatgag    540
gaggtcatca acctcattcg aaccaagaaa actgtgtcca tcaaagtgag acacatcggc    600
ctgatccccg tgaaaagctc tcctgatgag cccctcactt ggcagtatgt ggatcagttt    660
gtgtcggaat ctggggcgt gcgaggcagc ctgggctccc ctggaaatcg ggaaaacaag    720
gagaagaagg tcttcatcag cctggtaggc tcccgaggcc ttggctgcag catttccagc    780
ggccccatcc agaagcctgg catctttatc agccatgtga aacctggctc cctgtctgct    840
gaggtgggat tggagatagg ggaccagatt gtcgaagtca atggcgtcga cttctctaac    900
ctggatcaca aggaggctgt aaatgtgctg aaaaatagcc gcagcctgac catctccatt    960
gtagctgcag ctgccgggga gctgttcatg acagaccggg agcggctggc agaggcgcgg   1020
cagcgtgagc tgcagcggca ggagcttctc atgcagaagc ggctggcgat ggagtccaac   1080
aagatcctcc aggagcagca ggagatggag cggcaaagga gaaagaaat tgcccagaag   1140
gcagcagagg aaaatgagag ataccggaag gagatggaac agattgtaga ggaggaagag   1200
aagtttaaga agcaatggga agaagactgg ggctcaaagg aacagctact cttgcctaaa   1260
accatcactg ctgaggtaca cccagtaccc cttcgcaagc caaagtgatt tccggaaata   1320
tgaggaaggc tttgaccccct actctatgtt caccccagag cagatcatgg ggaaggatgt   1380
ccggctccta cgcatcaaga aggagggatc cttagacctg gccctggaag gcggtgtgga   1440
ctcccccatt gggaaggtgg tcgtttctgc tgtgtatgag cggggagctg ctgagcggca   1500
tggtggcatt gtgaaagggg acgagatcat ggcaatcaac ggcaagattg tgacagacta   1560
caccctggct gaggctgacg ctgccctgca gaaggcctgg aatcagggcg gggactggat   1620
cgaccttgtg gttgccgtct gcccccccaaa ggagtatgac gatgagctga ccttcttgct   1680
gaagtccaaa aggggaaacc aaattcacg gttaggaaac agtgagctcc ggccccacct   1740
cgtgaacaca aagcctcgga ccagccttga gagaggccac atgacacaca ccagatggca   1800
tccttgggac ctgaatctat cacccaggaa tctcaaactc cctttggccc tgaaccaggg   1860
ccagataagg aacagctcgg gccacttttt tgaaggccaa tgtggaggaa agggagcagc   1920
cagccgtttg ggagaagatc tcaaggatcc agactctcat tcctttcctc tggcccagtg   1980
aatttggtct ctcccagctt tgggggactc cttccttgaa ccctaataag accccactgg   2040
agtctctctc tctccatccc tctcctctgc cctctgctct aattgctgcc aggattgtca   2100
ctccaaacct tactctgagc tcattaataa aataaacaga tttatttcc agcttaaaaa   2160
aa                                                                  2162
```

<210> SEQ ID NO 6
<211> LENGTH: 1789
<212> TYPE: DNA
<213> ORGANISM: Homo Sapiens

<400> SEQUENCE: 6

-continued

| | |
|---|---|
| cttctggatg catccgagaa gctaaaactt acttatgagg aaaagtgtga aattgaggaa | 60 |
| tcccaattga agttttgag gaacgactta gctgaatatc agagaacttg tgaagatctt | 120 |
| aaagagcaac taaagcataa agaatttctt ctggctgcta atacttgtaa ccgtgttggt | 180 |
| ggtctttgtt tgaaatgtgc tcagcatgaa gctgttcttt cccaaaccca tactaatgtt | 240 |
| catatgcaga ccatcgaaag actggttaaa gaaagagatg acttgatgtc tgcactagtt | 300 |
| tccgtaagga gcagcttggc agatacgcag caaagagaag caagtgctta tgaacaggtg | 360 |
| aaacaagttt tgcaaatatc tgaggaagcc aattttgaaa aaccaaggc tttaatccag | 420 |
| tgtgaccagt tgaggaagga gctggagagg caggcggagc gacttgaaaa agaacttgca | 480 |
| tctcagcaag agaaaagggc cattgagaaa gacatgatga aaaaggaaat aacgaaagaa | 540 |
| agggagtaca tgggatcaaa gatgttgatc ttgtctcaga atattgccca actggaggcc | 600 |
| caggtggaaa aggttacaaa ggaaaagatt tcagctatta atcaactgga ggaaattcaa | 660 |
| agccagctgg cttctcggga atggatgtc acaaggtgt gtggagaaat gcgctatcag | 720 |
| ctgaataaaa ccaacatgga gaaggatgag gcagaaaagg agcacagaga gttcagagca | 780 |
| aaaactaaca gggatcttga aattaaagat caggaaatag agaaattgag aatagaactg | 840 |
| gatgaaagca acaacacttt ggaacaggag cagcagaagg cagccctggc cagagaggag | 900 |
| tgcctgagac taacagaact gctgggcgaa tctgagcacc aactgcacct caccagacag | 960 |
| gaaaaagata gcattcagca gagctttagc aaggaagcaa aggcccaagc ccttcaggcc | 1020 |
| cagcaaagag agcaggagct gacacagaag atacagcaaa tggaagccca gcatgacaaa | 1080 |
| actgaaaatg aacagtattt gttgctgacc tcccagaata cattttttgac aaagttaaag | 1140 |
| gaagaatgct gtacattagc caagaaactg gaacaaatct ctcaaaaaac cagatctgaa | 1200 |
| atagctcaac tcagtcaaga aaaaaggtat acatatgata aattgggaaa gttacagaga | 1260 |
| agaaatgaag aattggagga acagtgtgtc cagcatggga gagtacatga gacgatgaag | 1320 |
| caaaggctaa ggcagctgga taagcacagc caggccacag cccagcagct ggtgcagctc | 1380 |
| ctcagcaagc agaaccagct tctcctggag aggcagagcc tgtcggaaga ggtggaccgg | 1440 |
| ctgcggaccc agttacccag catgccacaa tctgattgct gacctggatg aacagagtg | 1500 |
| aaataaatga attacaaaga gatatttaca ttcatctggt ttagacttaa tatgccacaa | 1560 |
| cgcaccacga ccttcccagg gtgacaccgc ctcagcctgc agtggggctg gtcctcatca | 1620 |
| acgcgggcgc tgtccccgca cgcagtcggg ctggagctgg agtctgactc tagctgagca | 1680 |
| gactcctggt gtatgttttc agaaatggct tgaagttatg tgtttaaatc tgctcattcg | 1740 |
| tatgctaggt tatacatatg attttcaata aatgaacttt ttaaagaaa | 1789 |

<210> SEQ ID NO 7
<211> LENGTH: 1306
<212> TYPE: DNA
<213> ORGANISM: Homo Sapiens

<400> SEQUENCE: 7

| | |
|---|---|
| aaaaatagcc gcagcctgac catctccatt gtagctgcag ctggccggga gctgttcatg | 60 |
| acagaccggg agcggctggc agaggcgcgg cagcgtgagc tgcagcggca ggagcttctc | 120 |
| atgcagaagc ggctggcgat ggagtccaac aagatcctcc aggagcagca ggagatggag | 180 |
| cggcaaagga gaaagaaat tgcccagaag gcagcagagg aaaatgagag ataccggaag | 240 |
| gagatggaac agattgtaga ggaggaagag aagtttaaga agcaatggga agaagactgg | 300 |
| ggctcaaagg aacagctact cttgcctaaa accatcactg ctgaggtaca cccagtaccc | 360 |

```
cttcgcaagc caaagtatga tcagggagtg gaacctgagc tcgagcccgc agatgacctg      420
gatggaggca cggaggagca gggagagcag gatttccgga aatatgagga aggctttgac      480
ccctactcta tgttcacccc agagcagatc atggggaagg atgtccggct cctacgcatc      540
aagaaggagg gatccttaga cctggccctg gaaggcggtg tggactcccc cattgggaag      600
gtggtcgttt ctgctgtgta tgagcgggga gctgctgagc ggcatggtgg cattgtgaaa      660
ggggacgaga tcatggcaat caacggcaag attgtgacag actacaccct ggctgaggct      720
gacgctgccc tgcagaaggc ctggaatcag gcgggggact ggatcgacct tgtggttgcc      780
gtctgccccc caaggagta tgacgatgag ctgaccttct tgctgaagtc caaaggggga      840
aaccaaattc acgcgttagg aaacagtgag ctccggcccc acctcgtgaa cacaaagcct      900
cggaccagcc ttgagagagg ccacatgaca cacaccagat ggcatccttg ggacctgaat      960
ctatcaccca ggaatctcaa actcccttg gccctgaacc agggccagat aaggaacagc     1020
tcgggccact ttttgaagg ccaatgtgga ggaaagggag cagccagccg tttgggagaa     1080
gatctcaagg atccagactc tcattccttt cctctggccc agtgaatttg gtctctccca     1140
gctttggggg actccttcct tgaaccctaa taagacccca ctggagtctc tctctctcca     1200
tccctctcct ctgccctctg ctctaattgc tgccaggatt gtcactccaa accttactct     1260
gagctcatta ataaataaa cagatttatt ttccagctta aaaaaa                     1306

<210> SEQ ID NO 8
<211> LENGTH: 2289
<212> TYPE: DNA
<213> ORGANISM: Homo Sapiens

<400> SEQUENCE: 8
cctggcccgg tcgcggtcgc ggctctttcc agctcctggc agccgggcac ccgaaggaac       60
gggtcgtgca acgacgcagc tggacctggc ccagccatgg accgaaaagt ggcccgagaa      120
ttccggcata aggtggattt ctgattgaa aatgatgcag agaaggacta tctctatgat      180
gtgctgcgaa tgtaccacca gaccatggac gtggccgtgc tcgtgggaga cctgaagctg      240
gtcatcaatg aacccagccg tctgcctctg tttgatgcca ttcggccgct gatcccactg      300
aagcaccagg tggaatatga tcagctgacc ccccggcgct ccaggaagct gaaggaggtg      360
cgtctggacc gtctgcaccc cgaaggcctc ggcctgagtg tgcgtggtgg cctggagttt      420
ggctgtgggc tcttcatctc ccacctcatc aaaggcggtc aggcagacag cgtcgggctc      480
caggtagggg acgagatcgt ccggatcaat ggatattcca tctcctcctg tacccatgag      540
gaggtcatca acctcattcg aaccaagaaa actgtgtcca tcaaagtgag acacatcggc      600 ctgatcccg tgaaaagctc tcctgatgag cccctcactt ggcagtatgt ggatcagttt      660
gtgtcggaat ctgggggcgt gcgaggcagc ctgggctccc ctggaaatcg ggaaaacaag      720
gagaagaagg tcttcatcag cctggtaggc tcccgaggcc ttggctgcag catttccagc      780
ggccccatcc agaagcctgg catctttatc agccatgtga aacctggctc cctgtctgct      840
gaggtgggat tggagatagg ggaccagatt gtcgaagtca tggcgtcga cttctctaac      900 ctggatcaca aggaggctgt aaatgtgctg aaaaatagcc gcagcctgac catctccatt      960
gtagctgcag ctggccggga gctgttcatg acagaccggg agcggctggc agaggcgcgg     1020
cagcgtgagc tgcagcggca ggagcttctc atgcagaagc ggctggcgat ggagtccaac     1080
aagatcctcc aggagcagca ggagatggag cggcaaagga gaaagaaat tgcccagaag     1140
```

-continued

```
gcagcagagg aaaatgagag ataccggaag gagatggaac agattgtaga ggaggaagag    1200
aagtttaaga agcaatggga agaagactgg ggctcaaagg aacagctact cttgcctaaa    1260
accatcactg ctgaggtaca cccagtaccc cttcgcaagc caaagtatga tcagggagtg    1320
gaacctgagc tcgagcccgc agatgacctg gatggaggca cggaggagca gggagagcag    1380
ccacaggaga tgttgaagag gatggtggtt tatcaagaca gcattcaaga caagatttcc    1440
ggaaatatga ggaaggcttt gacccctact ctatgttcac cccagagcag atcatgggga    1500
aggatgtccg gctcctacgc atcaagaagg agggatcctt agacctggcc ctggaaggcg    1560
gtgtggactc ccccattggg aaggtggtcg tttctgctgt gtatgagcgg ggagctgctg    1620
agcggcatgg tggcattgtg aaagggggacg agatcatggc aatcaacggc aagattgtga    1680
cagactacac cctggctgag gctgacgctg ccctgcagaa ggcctggaat cagggcgggg    1740
actggatcga ccttgtggtt gccgtctgcc ccccaaagga gtatgacgat gagctgacct    1800
tcttgctgaa gtccaaaagg ggaaaccaaa ttcacgcgtt aggaaacagt gagctccggc    1860
cccacctcgt gaacacaaag cctcggacca gccttgagag aggccacatg acacacacca    1920
gatggcatcc ttgggacctg aatctatcac ccaggaatct caaactccct ttggccctga    1980
accagggcca gataaggaac agctcgggcc actttttttga aggccaatgt ggaggaaagg    2040
gagcagccag ccgtttggga gaagatctca aggatccaga ctctcattcc tttcctctgg    2100
cccagtgaat ttggtctctc ccagctttgg gggactcctt ccttgaaccc taataagacc    2160
ccactggagt ctctctctct ccatccctct cctctgccct ctgctctaat tgctgccagg    2220
attgtcactc caaaccttac tctgagctca ttaataaaat aaacagattt attttccagc    2280
ttaaaaaaa                                                            2289
```

ISOLATED NUCLEIC ACID MOLECULES ASSOCIATED WITH COLON CANCER AND METHODS FOR DIAGNOSING AND TREATING COLON CANCER

FIELD OF THE INVENTION

This invention relates to the isolation of genes associated with colon cancer, methods of diagnosing colon cancer using these, as well as other genes which are known, as well as therapeutic approaches to treating such conditions.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines. Transfectants are screened for the expression of tumor antigens via their ability to provoke reactions by anti-tumor cytolytic T cell clones. The biochemical approach, exemplified by, e.g., Mandelboim, et al., Nature 369: 69 (1994) incorporated by reference, is based on acidic elution of peptides which have bound to MHC-class I molecules of tumor cells, followed by reversed-phase high performance liquid chromography (HPLC). Antigenic peptides are identified after they bind to empty MHC-class I molecules of mutant cell lines, defective in antigen processing, and induce specific reactions with cytolytic T-lymphocytes ("CTLs"). These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; second, they depend on the establishment of CTLs with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. Pat. No. 5,698,396, and U.S. Pat. No. 5,698,396, filed on Jun. 7, 1995 and Jan. 3, 1996, respectively. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

The SEREX methodology has now been applied to colon cancer samples. Several nucleic acid molecules have been newly isolated and sequenced, and are now associated with stomach cancer. Further, a pattern of expression involving these, as well as previously isolated genes has been found to be associated with colon cancer. These results are the subject of this application, which is elaborated upon in the disclosure which follows.

DETAILED DESCRIPTION OF PREFERRED EMBODIMENTS

EXAMPLE 1

Tumor samples were obtained as surgical samples, and were frozen at −80° C. until ready for use.

Total RNA was then isolated from the samples, using the well known guanidium thiocyanate method of Chirgwin, et al., Biochemistry 18: 5294–5299 (1979), incorporated by reference. The thus obtained total RNA was then purified to isolate all poly A$^+$ RNA, using commercially available products designed for this purpose.

The poly A$^+$ RNA was then converted into cDNA, and ligated into λZAP, a well known expression vector.

Three cDNA libraries were constructed in this way, using colorectal carcinoma samples. A fourth library, also from colorectal carcinoma, was prepared, albeit in a different way. The reasons for this difference will be clear in the examples, infra.

The fourth library was an IgG subtraction library, prepared by using a subtraction partner, generated by PCR amplification of a cDNA clone which encoded an IgG molecule. See, e.g., Ace et al, Endocrinology 134: 1305–1309 (1994), and incorporated by reference in its entirety.

This is done to eliminate any false, positive signals resulting from interaction of cDNA clones which encode IgG, with the anti-human IgG used in the assay, as described infra. PCR product was biotinylated, and hybridized with denatured second strand cDNA, at 68° C. for 18 hours. Biotinylated hybrid molecules were coupled to streptavidin, and then removed by phenol chloroform extraction. Any remaining cDNA was also ligated into λZAP. All libraries were amplified, prior to immunoscreening discussed infra.

EXAMPLE 2

Immunoscreening was carried out, using sera obtained from patients undergoing routine diagnostic and therapeutic procedures. The sera were stored at −70° C. prior to use. Upon thawing, the sera were diluted at 1:10 in Tris buffered saline (pH 7.5), and were then passed through Sepharose 4B columns. First, the sera were passed through columns which had *E. coli* Y1090 lysates coupled thereto, and then lysates from bacteriophage infected *E. coli* BNN97 lysates. Final serum dilutions were then prepared in 0.2% non-fat dried milk/Tris buffered saline.

The method of Sahin et al., Proc. Natl. Acad. Sci. USA 92: 11810–11813 (1995), and allowed U.S. Pat. No. 5,698,396, both of which are incorporated by reference, was used, with some modifications. Specifically recombinant phage at a concentration of 4×10³ phages per 15 cm plate (pfus), were amplified for six hours, after which they were transferred to nitrocellulose membranes for 15 hours. Then, the membranes were blocked with 5% nonfat dried milk.

As an alternative to the IgG subtraction, discussed supra, membranes were prescreened in a 1:2000 dilution of peroxidase conjugated, Fc fragment specific goat anti-human IgG, for one hour, at room temperature. Color was developed using 3,3-diaminobenzidine tetrahydrochloride, which permitted scoring of IgG encoding clones.

Membranes were then incubated in 1:100 dilutions of autologous sera, which had been pretreated with the Sepharose 4B columns, as described supra. The filters were then incubated, in a 1:3000 dilution of alkaline phosphatase conjugated Fc fragment specific, goat anti-human IgG, for one hour, at room temperature. The indicator system 4-nitroblue tetrazolium chloride/5-bromo-4-chloro-3-indolyl-phosphate was then added, and color development assessed. Any positive clones were subcloned, and retested, except the tine on the nitrocellulose membrane was reduced to three hours. A total of forty-eight positive clones were identified.

Analysis of probes for SEQ ID NOS: 1 and 2 confirmed their universal expression.

EXAMPLE 3

Example 2 described work using autologous serum. The positive clones were then rescreened, using allogeneic serum, following the same method discussed supra, in example 2, except IgG prescreening was omitted. The allogeneic sera was obtained from sixteen normal blood donors, and twenty nine patients who had been diagnosed with colorectal cancer.

The analysis with the two types of serum revealed that fourteen reacted with a subset of sera from normal and cancer patients, twenty-eight only with autologous sera, and six with both allogeneic and autologous sera. Over 60% of the allogeneic serum samples tested reacted with at least one of these positive clones. About 20% reacted with two or more.

EXAMPLE 4

In view of the results described in example 3, further experiments were carried out using serum samples from patients with other forms of cancer, i.e., renal cancer (13 samples), lung cancer (23 samples), and breast cancer (10 samples). The results are set forth in Table I which follow:

| Clone Number | Normal Sera | Colon Cancer | Renal Cancer | Lung Cancer | Breast Cancer |
|---|---|---|---|---|---|
| NY-Co-8 | 0/16 | 8/29 | 1/13 | 0/23 | 0/10 |
| NY-Co-9 | 0/16 | 5/29 | 1/13 | 1/23 | 0/10 |
| NY-Co-13 | 0/16 | 5/29 | 0/13 | 0/23 | 0/10 |
| NY-Co-16 | 0/16 | 3/29 | 0/13 | 0/23 | 0/10 |
| NY-Co-20 | 0/16 | 4/29 | 0/13 | 0/23 | 0/10 |
| NY-Co-38 | 0/16 | 4/29 | 3/13 | 0/23 | 1/10 |

EXAMPLE 5

Following the screening work described supra, the cDNA inserts were purified and sequenced, following standard methods.

Of the six clones which were identified as being reactive with autologous and allogeneic cancer serum, and not with normal serum, two were found to be identical to previously identified molecules. Four others were found to have little or no homology to known sequences. These are presented as SEQ ID NOS: 1–4. Of twenty seven allogeneic colon cancer serum samples tested, 67% reacted with at least one of these antigens.

EXAMPLE 6

The expression pattern of mRNA corresponding to SEQ ID NOS: 1, 2 and 4, as well as other sequences identified via the preceding examples was determined. To do this, RT-PCR was carried out on a panel of RNA samples, taken from normal tissue. The panel contained RNA of lung, testis, small intestine, colon, breast, liver and placenta tissues. The RNA was purchased from a commercial source. RNA from a colon tumor sample was also included. All samples were set up for duplicate runs, so that genomic DNA contamination could be accounted for. In the controls, no reverse transcriptase was used.

Primers were designed which were specific for the cDNA, which would amplify 5'-fragments, from 300 to 400 base pairs in length. The PCR reactions were undertaken at an annealing temperature of 68° C. Where appropriate, 5' and 3'-RACE reactions were undertaken, using gene specific primers, and adapter primers, together with commercially available reagents. Specifically, SEQ ID NOS: 2 and 4 were tested using RACE. The resulting products were subcloned into vector pCR 2.1, screened via PCR using internal primers, and then sequenced.

SEQ ID NOS: 1 and 2 were found to be amplified in all tissues tested. SEQ ID NO: 4 was found in colon tumor, colon metastasis, gastric cancer, renal cancer and colon cancer cell lines Colo 204 and HT29, as well as in normal colon, small intestine, brain, stomach, testis, pancreas, liver, lung, heart, fetal brain, mammary gland, bladder, adrenal gland tissues. It is was not found in normal uterine, skeletal muscle, peripheral blood lymphocytes, placental, spleen thymus, or esophagus tissue, nor in lung cancer.

The analysis also identified differential expression of a splice variant of SEQ ID NO: 4, i.e., SEQ ID NO: 5. When the two sequences were compared, it was found that SEQ ID NO: 4 encodes a putative protein of 652 amino acids, and molecular weight of 73,337 daltons. SEQ ID NO: 5, in contrast, lacks an internal 74 base pairs, corresponding to nucleotides 1307–1380 of SEQ ID NO: 4. The deletion results in formation of a stop codon at the splice function, and a putative protein of 404 amino acids, and molecular weight 45,839. The missing segment results in the putative protein lacking a PEST protein degradation sequence, thereby suggesting a longer half life for this protein.

In additional experiments, primers designed not to differentiate between SEQ ID NOS: 4 and 5 resulted in almost universal amplification (placenta being the only exception). In contrast, when primers specific for SEQ ID NO: 5 were used differences were seen in normal pancreatic, liver, lung, heart, fetal brain, mammary gland, bladder, and adrenal gland tissue, where there was no expression of SEQ ID NO: 5 found.

EXAMPLE 7

Northern blotting was also carried out for SEQ ID NOS: 1, 2, 4 and 5. To do this, the same commercially available RNA libraries discussed supra were used.

Samples (2 ug) of polyA+ RNA were analyzed from these samples, using random, $^{32}$P labelled probes 300–360 nucleotides in length, obtained from PCR products. These probes were hybridized to the RNA, for 1.5 hours, at 68° C., followed by two washes at 0.1×SSC, 0.1% SDS, 68° C., for 30 minutes each time.

SEQ ID NOS: 1 and 2 were again found to be universally expressed.

EXAMPLE 8

Further screening identified additional isoforms of SEQ ID NOS: 1 and 4. These are set forth as SEQ ID NOS: 6, 7 and 8. The isoform represented by SEQ ID NO: 6 is a naturally occurring splice variant of SEQ ID NO: 1, found in normal colon. SEQ ID NO: 7, which is an isoform of SEQ ID NO: 4, was found in brain tissue, primarily spinal chord and medulla. SEQ ID NO: 8, was found in normal kidney and in colon tumors, metastasized colon cancer, gastric cancer, and in colon cancer cell line Colo 205. It was not found in any normal tissue other than kidney.

The foregoing examples demonstrate several features of the invention. These include diagnostic methods for determining presence of transformed cells, such as colon cancer cells, in a sample. The sample may contain whole cells or it may be, e.g., a body fluid sample, or an effusion, etc., where the sample may contain cells, but generally will contain shed antigen. The experiments indicate that there is a family of proteins, expression of which is associated with colon cancer. Hence, the invention involves, inter alia, detecting at least two of the proteins encoded by any of SEQ ID NOS: 1–5 wherein, presence of these is indicative of a pathology, such as colon cancer or other type of related condition. Exemplary of the type of diagnostic assays which can be carried out are immunoassays, amplification assays (e.g., PCR), or, what will be referred to herein as a "display array". "Display array" as used herein refers to a depiction of the protein profile of a given sample. Exemplary of such displays are 2-dimensional electrophoresis, banding patterns such as SDS-gels, and so forth. Thus, one aspect of the invention involves diagnosing colon cancer or a related condition by determining protein display of a sample, wherein a determination of at least one of the proteins, or expression of their genes, is indicative of colon cancer or a related condition. There are many ways to carry out these assays. For example, as indicated herein, antibodies to the proteins were found in patient samples. One can assay for these antibodies using, e.g., the methodology described herein, or by using a purified protein or proteins or antigenic fragment thereof, and so forth. One can also assay for the protein itself, using antibodies, which may be isolated from samples, or generated using the protein and standard techniques. This antibodies can then be labelled, if desired, and used in standard immunoassays. These antibodies or oligonucleotide probes/primers may also be used to examine biopsied tissue samples, e.g., to diagnose precancerous conditions, early stage cancers, and so forth.

Similarly, any and all nucleic acid hybridization systems can be used, including amplification assays, such as PCR, basic probe hybridization assays, and so forth. The antibodies, such as polyclonal antibodies, monoclonal antibodies, the hybridomas which produce them, recombinantly produced antibodies, binding fragments of these, hybridization kits, DNA probes, and so forth, are all additional features of the invention.

Any of these assays can also be used in progression/regression studies. One can monitor the course of an abnormality such as colon cancer which involve expression of any one of the proteins, the expression of which is governed by the nucleic acid molecules SEQ ID NOS: 1–5, simply by monitoring levels of the protein, its expression, and so forth using any or all of the methods set forth supra.

As has been indicated supra, the isolated nucleic acid molecules which comprise the nucleotide sequences set forth in SEQ ID NOS: 1–5 are new, in that they have never been isolated before. These nucleic acid molecules may be used as a source to generate colon cancer specific proteins and peptides derived therefrom, and oligonucleotide probes which can themselves be used to detect expression of these genes. Hence, a further aspect of the invention is an isolated nucleic acid molecule which comprises any of the nucleotide sequences set forth in SEQ ID NOS: 1–5, or molecules whose complements hybridize to one or more of these nucleotide sequences, under stringent conditions, expression vectors comprising these molecules, operatively linked to promoters, cell lines and strains transformed or transfected with these, and so forth. "Stringent conditions", is used herein, refers to condition such as those specified in U.S. Pat. No. 5,342,774, i.e., 18 hours of hybridization at 65° C., followed by four one hour washes at 2×SSC, 0.1% SDS, and a final wash at 0.2×SSC, more preferably 0.1×SSC, 0.1% SDS for 30 minutes, as well as alternate conditions which afford the same level of stringency, and more stringent conditions.

It should be clear that these methodologies may also be used to track the efficacy of a therapeutic regime. Essentially, one can take a baseline value for the protein or proteins being tested, using any of the assays discussed supra, administer a given therapeutic, and then monitor levels of the protein or proteins thereafter, observing changes in protein levels as indicia of the efficacy of the regime.

The identification of the proteins and nucleic acid molecules set forth herein as being implicated in pathological conditions such as colon cancer also suggests a number of therapeutic approaches to such conditions. The experiments set forth supra establish that antibodies are produced in response to expression of these proteins, suggesting their use as a vaccine. Hence, a further embodiment of the invention is the treatment of conditions which are characterized by expression of one or more of the subject proteins, via immunotherapeutic approaches. One of these approaches is the administration of an amount of one or more these proteins, or an immunogenic peptide derived therefrom in an amount sufficient to provoke or augment an immune response. The proteins or peptides may be combined with one or more of the known immune adjuvants, such as saponins GM-CSF interleukins, and so forth. If the peptides are too small to generate a sufficient antibody response, they can be coupled to the well known conjugates used to stimulate responses.

Similarly, the immunotherapeutic approaches include administering an amount of inhibiting antibodies sufficient to inhibit the protein or proteins. These antibodies may be, e.g., antibodies produced via any of the standard approaches elaborated upon supra.

T cell responses may also be elicited by using peptides derived from the proteins which then complex, non-covalently, with MHC molecules, thereby stimulating proliferation of cytolytic T cells against any such complexes in the subject. It is to be noted that the T cells may also be elicited in vitro, and then reperfused into the subject being treated.

Note that the generation of T cells and/or antibodies can also be accomplished by administering cells, preferably treated to be rendered non-proliferative, which present relevant T cell or B cell epitopes for response.

The therapeutic approaches may also include gene therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the well known BCG vaccine, and so forth.

An additional DNA based therapeutic approach is the use of a vector which comprises one or more nucleotide sequences, preferably a plurality of these, each of which encodes an immunoreactive peptide derived from the expressed proteins. One can combine these peptides expressing sequences in all possible variations, such as one from each protein, several from one or more protein and one from each of the additional proteins, a plurality from some and none from others, and so forth.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule selected from the group consisting of:
   (a) nucleic acid molecules which encode a cancer associated antigen, and which comprise a nucleotide sequence, the complementary sequence of which hybridizes, under stringent conditions, to at least one second nucleic acid molecule comprising a nucleotide sequence selected from the group consisting of the nucleotide sequences set forth as SEQ ID NOs: 1, 2, 3, 4, and 5,
   (b) nucleic acid molecules that differ from the nucleic acid molecules of (a) in codon sequence due to the degeneracy of the genetic code, and (c) complements of (a) or (b).

2. The isolated nucleic acid molecule of claim 1, wherein the nucleotide sequence of the second nucleic acid molecule is SEQ ID NO:1.

3. The isolated nucleic acid molecule of claim 1, wherein the nucleotide sequence of the second nucleic acid molecule is SEQ ID NO:2.

4. The isolated nucleic acid molecule of claim 1, wherein the nucleotide sequence of the second nucleic acid molecule is SEQ ID NO:3.

5. The isolated nucleic acid molecule of claim 1, wherein the nucleotide sequence of the second nucleic acid molecule is SEQ ID NO:4.

6. The isolated nucleic acid molecule of claim 1, wherein the nucleotide sequence of the second nucleic acid molecule is SEQ ID NO:5.

7. A composition comprising the isolated nucleic acid molecule of claim 1, and a physiologically acceptable carrier.

8. An expression vector comprising the isolated nucleic acid molecule of claim 1, operably linked to a promoter.

9. A cell line or cell strain comprising the expression vector of claim 8.

10. A cell line or cell strain comprising the isolated nucleic acid molecule of claim 1.

11. The isolated nucleic acid molecule of claim 1, which comprises a nucleotide sequence selected from the group consisting of the nucleotide sequences set forth as SEQ ID NOs: 1, 2, 3, 4, and 5.

12. The isolated nucleic acid molecule of claim 11, wherein the nucleotide sequence comprises SEQ ID NO:1.

13. The isolated nucleic acid molecule of claim 11, wherein the nucleotide sequence comprises SEQ ID NO:2.

14. The isolated nucleic acid molecule of claim 11, wherein the nucleotide sequence comprises SEQ ID NO:3.

15. The isolated nucleic acid molecule of claim 11, wherein the nucleotide sequence comprises SEQ ID NO:4.

16. The isolated nucleic acid molecule of claim 11, wherein the nucleotide sequence comprises SEQ ID NO:5.

* * * * *